United States Patent [19]

Brown et al.

[11] Patent Number: 4,824,858

[45] Date of Patent: Apr. 25, 1989

[54] 1,3-DIOXOLANE-5-YL-HEXENOIC ACID DERIVATIVES

[75] Inventors: George R. Brown, Wilmslow; Michael J. Smithers, Macclesfield, both of United Kingdom

[73] Assignee: Imperial Chemical Industries PLC, London, England

[21] Appl. No.: 861,335

[22] Filed: May 9, 1986

[30] Foreign Application Priority Data

May 10, 1985 [GB] United Kingdom ............... 8511896
Dec. 30, 1985 [GB] United Kingdom ............... 8531893

[51] Int. Cl.$^4$ .................. A61K 31/335; C07D 319/06
[52] U.S. Cl. ..................................... 514/336; 549/375; 549/373; 549/370; 549/362; 549/350; 548/268; 548/254; 548/253; 548/252; 546/268; 514/452; 514/450; 514/382
[58] Field of Search ............... 549/375, 350, 362, 370, 549/373; 548/252, 253, 254; 546/268; 514/452, 450, 382, 336

[56] References Cited

U.S. PATENT DOCUMENTS 4,567,197  1/1986  Brewster et al. .................. 514/452

FOREIGN PATENT DOCUMENTS 0094239 11/1983  European Pat. Off. .
0142323  5/1985  European Pat. Off. .
0142324  5/1985  European Pat. Off. .
0145260  6/1985  European Pat. Off. .

*Primary Examiner*—Nicky Chan
*Attorney, Agent, or Firm*—Cushman, Darby & Cushman

[57] ABSTRACT

The invention describes novel (2-styryl-, 2-naphthyl- and 2-phenethyl-4-o-hydroxyphenyl-1,3-dioxan-5-yl)alkenoic acids and related tetrazoles and sulphonamides, of the formula I wherein Q completes a benzene or pyridine ring, Y is vinylene, Z is carboxy, 1 (H)-tetrazol-5-yl or a group of the formula —CO.NHSO$_2$R$^6$, and R$^1$, R$^2$, R$^3$, R$^4$, R$^5$, R$^6$, A$^1$, A$^2$, n and m have the meanings defined in the specification, and pharmaceutically acceptable salts thereof, for use in conjunction with their pharmaceutical compositions in treating certain pulmonary and/or vascular disorders. The invention also describes various processes and intermediates for the manufacture of the novel compounds.

8 Claims, No Drawings

1,3-DIOXOLANE-5-YL-HEXENOIC ACID DERIVATIVES

This invention concerns novel alkene derivatives and, more particularly, novel (2-styryl-, 2-naphthyl- and 2-phenethyl-4-o-hydroxyphenyl-1,3-dioxan-5-yl)alkenoic acids and related compounds, which antagonise one or more of the actions of thromboxane $A_2$ (hereafter referred to as "$TXA_2$") and which are of value as therapeutic agents.

It is known that $TXA_2$ is a potent aggregator of blood platelets and a powerful vasconstrictor. $TXA_2$ is also a potent constrictor of bronchial and tracheal smooth muscle. $TXA_2$ may therefore be involved in a wide variety of disease conditions, for example ischaemic heart disease such as myocardial infarction, angina, cerebrovascular disease such as transient cerebral ischaemia, migraine and stroke, peripheral vascular disease such as atherosclerosis, microangiopathy, hypertension and blood clotting defects due to lipid imbalance, and pulmonary disease such as pulmonary embolism, bronchial asthma, bronchitis, pneumonia, dyspnoea and emphysema. Accordingly, compounds which antagonise the actions of $TXA_2$ may be expected to have therapeutic value in the prevention or treatment of any one or more of the above mentioned diseases or any other disease conditions in which it is desirable to antagonise the actions of $TXA_2$.

It is known that certain 4-phenyl-1,3-dioxan-5-ylalkenoic acids possess $TXA_2$ antagonist properties (European patent application, publication No. 94239).

According to the invention there is provided a [2,4,5-cis]-dioxane of the formula I (set out hereinafter) wherein $A^1$ and $A^2$ are hydrogen or together form a direct link; $R^1$ and $R^2$ are independently hydrogen, (1-4C)alkyl or phenyl optionally bearing 1 or 2 substituents independently selected from halogeno, nitro, cyano, trifluoromethyl and (1-4C)alkyl; $R^3$ is hydrogen or, together with $A^1$, forms vinylene, ethylene or oxymethythene; $R^4$ and $R^5$ are independently selected from hydrogen, halogeno, (1-4C)alkyl, (1-4C)alkoxy, nitro, cyano, trifluoromethyl, hydroxy, (1-4C)alkanoylamino and (2-4C)alkanoyloxy, or $R^4$ and $R^5$ together form (1-4C)alkylenedioxy attached to adjacent carbon atoms on Q; Y is or vinylene; n is 1 or 2; m is 1, 2 or 3; Q, in conjunction with its adjoining carbon atoms (shown with an asterisk in formula I hereinafter), completes a benzene or pyridine ring; and Z is carboxy, 1(H)-tetrazol-5-yl or a group of the formula $CO.NH.SO_2R^6$ wherein $R^6$ is (1-6C)alkyl, benzyl or phenyl, the latter two of which may optionally bear a halogeno, (1-4C)alkyl, (1-4C)alkoxy, nitro, cyano or trifluoromethyl substituent; or a pharmaceutically acceptable salt thereof.

The compounds of formula I contain at least three asymmetric carbon atoms and may exist and be isolated in racemic and optically active forms. In addition, the compounds of formula I contain 1 or 2 exocyclic vinylene groups and may exist, and be isolated, in separate stereoisomeric forms ('E' and 'Z'). It is to be understood that the invention includes any racemic, optically active or stereoisomeric form, or mixture thereof, which is capable of antagonising one or more of the actions of $TXA_2$, it being well known in the art how to prepare individual optical isomers (for example by synthesis from optically active starting materials or resolution of a racemic form) and individual 'E' and 'Z' stereoisomers (for example by synthesis from appropriate starting materials or by chromatographic separation of a mixture of isomers), and how to determine the $TXA_2$ antagonist properties using the standard tests described hereafter.

A preferred value for n is 1 and for m is 2 or 3.

A particular value for $R^1$ or $R^2$ when it is (1-4C)alkyl is, for example, methyl or ethyl.

A particular value for $R^6$ when it is (1-6C)alkyl is, for example, methyl, ethyl, propyl or isopropyl.

Particular values for optional substituents $R^4$ and $R^5$, or for substituents present as part of $R^1$, $R^2$ or $R^6$ when they are optionally substituted phenyl or benzyl, as defined above, include, for example:
for halogeno: fluoro, chloro or bromo;
for (1-4C)alkyl: methyl or ethyl;
for (1-4C)alkoxy: methoxy or ethoxy;
for (1-4C)alkanoylamino: formamido or acetamido;
for (1-4C)alkylenedioxy: methylenedioxy or ethylenedioxy.

Two groups of compounds of the invention of particular interest comprise styryl compounds of the formula IIa and naphthyl compounds of the formula IIb respectively, wherein $R^1$ and $R^2$ are independently hydrogen or (1-4C)alkyl, $R^4$ and $R^5$ are independently selected from hydrogen, halogeno (such as fluoro, chloro and bromo), (1-4C)alkyl (such as methyl), (1-4C)alkoxy (such as methoxy), hydroxy, nitro, cyano and trifluoromethyl, or $R^4$ and $R^5$ together form methylenedioxy; p is 2 or 3; and Z has the meanings given above; together with the pharmaceutically acceptable salts thereof.

It will be appreciated that the 2-styryl compounds of formula IIa may exist in the 'E' or 'Z' stereoisomeric form. However, in general, the 'E' 2-styryl stereoisomeric (or trans) form is preferred.

A preferred value for Z is, for example, carboxy. A preferred value for p is 2.

A preferred value for Y is cis-vinylene i.e. the 'Z' sterioisomeric form.

Specific compounds of the invention are described in the accompanying Examples. However, illustrative compounds of particular interest are the carboxylic acids described in Examples 1 and 7, or a pharmaceutically acceptable salt thereof.

Particular pharmaceutically acceptable salts of compounds of formula I are, for example, alkali metal and alkaline earth metal salts, such as lithium, sodium, potassium, magnesium and calcium salts, aluminium and ammonium salts, and salts with organic amines and quaternary bases, forming physiologically acceptable cations, such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

The compounds of formula I may be manufactured by conventional procedures of organic chemistry well known in the art for the manufacture of structurally analogous compounds. Such procedures are provided as a further aspect of the invention and are illustrated by the following processes in which $R^1$, $R^2$, $R^3$, $R^4$, $R^5$, $R^6$, $A^1$, $A^2$, Q, Y, Z, n, m and p have any of the meanings herein above:

(a) An aldehyde of the formula III is reacted with a Witting reagent of the formula IVa, IVb or IVc wherein R' is (1-6C)alkyl or aryl (especially phenyl) and $M^+$ is a cation, for example an alkali metal cation, such as the lithium, sodium or potassium cation.

The process in general produces compounds of formula I in which the substituents adjacent to the double bond have predominantly cis-relative stereochemistry i.e. the 'Z' isomer. However the compounds of formula I having trans-relative stereochemistry may also be obtained from the process by conventional separation of the mixture of cis- and trans-isomers first obtained.

The process is conveniently performed in a suitable solvent or diluent, for example an aromatic solvent such as benzene, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, $-80°$ C. to 40° C., but is conveniently performed at or near room temperature, that is in the range 0° to 35° C.

(b) For a compound of formula I wherein Z is 1(H)-tetrazol-5-yl, a nitrile of the formula V is reacted with an azide.

A particularly suitable azide is, for example, an alkali metal azide such as sodium or potassium azide, preferably together with an ammonium halide, for example ammonium chloride, ammonium bromide or triethylammonium chloride. The process is preferably carried out in a suitable polar solvent, for example N,N-dimethylformamide or N-methylpyrrolidone and, conveniently, at a temperature in the range, for example, 50° to 160° C.

(c) A phenol derivative of the formula VI, wherein R" is a suitable protecting group, for example (1–6C)alkyl (such as methyl or ethyl), acyl (such as acetyl, benzoyl, methanesulphonyl or p-toluene-sulphonyl), allyl, tetrahydropyran-2-yl or trimethylsilyl, is deprotected.

The precise deprotection conditions used depend on the nature of the protecting group R". Thus, for example, when it is methyl or ethyl the deprotection may be carried out by heating the sodium thioethoxide in a suitable solvent (such as N,N-dimethylformamide or 1,3-dimethyl-3,4,5,6-tetrahydro-2(1H)-pyrimidinone) at a temperature in the range, for example, 60°–160° C. Alternatively, an ethyl or methyl protecting group may be removed by reaction with lithium diphenylphosphide in a suitable solvent (such as tetrahydrofuran or t-butyl methyl ether) at a temperature in the range, for example, 0°–60° C. When the protecting group is acyl it may be removed, for example, by hydrolysis in the presence of a base (such as sodium or potassium hydroxide) in a suitable aqueous solvent [such as an aqueous (1–4C)alkanol] at a temperature in the range, for example, 0°–60° C. When the protecting group is allyl or tetrahydropyran-2-yl it may be removed, for example, by treatment with strong acid such as trifluoroacetic acid and when it is trimethylsilyl, it may be removed, for example, by reaction with aqueous tetrabutylammonium fluoride or sodium fluoride, using a conventional procedure.

(d) An erythro-diol derivative of the formula VII, wherein one of $Q^1$ and $Q^2$ is hydrogen and the other is hydrogen or a group of the formula $-CR_aR_b.OH$ (wherein $R_a$ and $R_b$ are the same or different (1–4C)alkyl), is reacted with an aldehyde of the formula IX, or an acetal, hemiacetal or hydrate thereof.

The aldehyde of formula IX [or its hydrate, or its acetal or hemiacetal with a (1–4C)alkanol (such as methanol or ethanol] is generally used in excess.

The reaction is generally performed in the presence of an acid catalyst, such as hydrogen chloride, hydrogen bromide, sulphuric acid, phosphoric acid, methanesulphonic acid, p-toluenesulphonic acid, or an acidic resin, conveniently in the presence of a suitable solvent or diluent, such as toluene, xylene or an ether, for example tetrahydrofuran, dibutyl ether, methyl t-butyl ether or 1,2-dimethoxyethane, and at temperature in the range, for example 0° to 80° C.

Those starting materials of formula VII wherein $Q^1$ and $Q^2$ are both hydrogen may be obtained, for example, by mild acid catalysed hydrolysis or alcoholysis of the dioxane ring of a compound of formula VIII wherein $R_a$ and $R_b$ are both alkyl, such as methyl or ethyl. The hydrolysis or alcoholysis will normally be carried out a temperature in the range 10° to 80° C. using an aqueous mineral acid such as hydrochloric acid, in an alkanol (such as ethanol or 2-propanol) or an ether (such as tetrahydrofuran), as solvent.

The starting materials of formula VII wherein one of $Q^1$ and $Q^2$ is hydrogen and the other is a group of the formula $-CR_aR_b.OH$ are intermediates in the above-mentioned formation of the starting materials of formula VII, wherein $Q^1$ and $Q^2$ are both hydrogen. However, said intermediates are not normally isolated or characterised. Accordingly, the invention also provides a modification of process (d) which comprises reacting a compound of formula VIII wherein one of $R_a$ and $R_b$ is hydrogen, methyl or ethyl and the other is methyl or ethyl, with an excess of an aldehyde of the formula IX, or an acetal, hemiacetal or hydrate thereof, in the presence of an acid-catalyst (such as one of those given above), conveniently at a temperature in the range, for example, 10° to 80° C. and optionally in the presence of a suitable solvent or diluent (such as one of those given above).

The starting materials for use in the above processes may be made by general procedures of organic chemistry, known for the preparation of structurally related compounds, for example by analogy with those procedures disclosed in European patent application, publication No. 94239.

The nitriles of formula V may be obtained, for example, by substituting the appropriate ylid of the formula $R'_3P=CH.(CH_2)_m.CN$ for the ylid of formula IV in the Wittig reaction described in process (a) above. The protected phenol derivatives of formula VI may be made, for example, by using an analogous procedure to process (a) above, using an aldehyde analogous to formula III but wherein the phenol group has been protected with the group R". The starting materials of formula VIII may be obtained using analogous procedures to those described in European patent application, publication No. 94239.

The necessary Wittig reagents of formula IV may be obtained by conventional procedures, for example by treating the corresponding phosphonium halides with a strong base, such as sodium hydride, lithium diisopropylamide, potassium t-butoxide or butyllithium. They are generally formed in situ just prior to carrying out the condensation process (a) above.

It will be understood that the compounds of formula I wherein Z is carboxy may also be obtained by other conventional procedures well known in the art for the production of carboxylic acids, for example by base-catalysed hydrolysis of the corresponding esters, for example, the lower alkyl esters. Such procedures are included within the invention.

When a compound of formula I wherein Z is a group of the formula $CO.NH.SO_2R^6$ is required, one of the above procedures (a), (c) or (d) is performed using the appropriate starting material of formula IVc, VI, VII or VIII.

The necessary starting materials of formula VI may conveniently be obtained by reacting the correponding protected acid of formula VI wherein Z is carboxy with a sulphonamide of the formula $H_2N.SO_2R^6$ and a suitable dehydrating agent, for example dicyclohexylcarbodiimide, optinally together with an organic base, for example 4-dimethylaminopyridine, in the presence of a suitable solvent or diluent, for example methylene chloride at a temperature in the range, 10°-50° C., but preferably at or near room temperature. Alternatively, a reactive derivative of the compound of formula VI wherein Z is carboxy, for example an acid halide (such as the acid chloride) may be reacted with an alkali metal salt (such as the sodium salt) of the appropriate sulphonamide, conveniently at or near room temperature and in a suitable solvent or diluent, for example an ether, N,N-dimethylformamide or methylene chloride.

When a salt of a compound of formula I is required, it may be obtained by reaction with the appropriate base affording a physiologically acceptable cation, or by any other conventional procedure.

Further, when an optically active form of a compound of formula I is required, one of the aforesaid processes is carried out using an optically active starting material. Alternatively, the racemic form of a compound of formula I may be reacted with an optically active form of a suitable organic base, for example ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said compound of formula I may be liberated by treatment with acid using a conventional procedure for example using an aqueous mineral acid such as dilute hydrochloric acid.

Many of the intermediates defined herein are novel, for example the phenol derivatives of formula VI, and are provided as further separate features of the invention.

As stated earlier, the compounds of formula I are antagonists of one or more of the actions of $TXA_2$, for example certain of its actions on blood platelets, the vasculature and/or the lung. The antagonism may be demonstrated in one or other of the following standard tests:

(a) The rabbit aortal strip model devised by Piper and Vane (*Nature*, 1969, 223, 29–35) using as agonist a freshly prepared sample of $TXA_2$, generated by addition of arachidonic acid (25 μg) to citrated, platelet rich rabbit plasma (250 μg) and allowing the mixture to aggregate fully over 90 seconds before use; alternatively the $TXA_2$ mimetic agent known as U46619 (described by R. L. Jones et alia, in "Chemistry, Biochemistry and Pharmacological Activity of Prostanoids" edited by S. M. Roberts and F. Scheinmann, at page 211, Pergamon Press, 1979) may be used as the agonist;

(b) a blood platelet aggregation test based on that described by Born (*Nature*, 1962, 194, 927–929) and involving:

(i) aggregating human, citrated platelet-rich plasma by addition of the $TXA_2$ mimetic agent U46619 so that a dose-response curve is generated;

(ii) generating a dose-response curve for U46619 stimulated platelet aggregation in the presence of increasing amounts of test compound (generally in the range, $10^{-5}M$ to $10^{-10}M$); and (iii) calculating a $K_B$ value indicating potency of $TXA_2$ antagonism for the test compound, averaged over several concentrations, from the calculated 50% response value for U46619 aggregation in the presence and absence of test compound; and (c) a bronchoconstriction test involving measuring the inhibition by test compound of the bronchoconstriction induced in the Konzett-Rossler, anaesthetised guinea-pig model (as modified by Collier and James, *Brit. J. Pharmacol.*, 1967, 30, 283–307) by intravenous administration of the $TXA_2$ mimetic agent, U46619 and involving:

(i) obtaining a cumulative dose-response curve to U46619 induced bronchoconstriction by intravenous administration of constant volumes of increasing concentrations of U46619 (0.2–4 μg/kg) in physiological saline solution and expressing bronchoconstriction as the maximum of that theoretically obtainable with no air flow to the test animal;

(ii) generating a cumulative dose-response curve to U46619 induced bronchoconstriction at 30 minute intervals for 3 hours after oral dosing of test compound; and (iii) calculating a dose-ratio for the test compound (that is the ratio of concentration of U46619 required to cause 50% bronchoconstriction in the presence and absence of test compound) indicating the potency of $TXA_2$ antagonism.

The antagonism of the effects of $TXA_2$ on the vasculature may be demonstrated, for example, in rats in the following manner:

Male rats (Alderley Park strain) are anaesthetised with sodium pentobarbital and blood pressure is monitored at the carotid artery. The $TXA_2$ mimetic agent U46619 is administered intravenously via the jugular vein at 5 μg/kg to induce a 20-30 mm Hg (2640-3970 pascal) increase in systolic blood pressure. The process is repeated twice to establish reproducibility of response. A test compound is then administered either intravenously via the jugular vein or orally via a cannula directly into the stomach and the or animal challenged with U46619 five minutes after dosing with test compound and then successively every ten minutes until the hypertensive effect of U46619 is no longer blocked. Further, the antagonism of the effects of $TxA_2$ in vivo may be demonstrated, for example, by assessing the effects of a test compound on the aggregation of blood platelets obtained after administration of test compound to a test animal such as a rabbit, rat, guinea pig or dog, using standard procedures similar to that described in (a) above. However, when the aggregation of dog platelets is being studied it is necessary to use a pre-determined, threshold concentration of the platelet aggregrant adenosine diphosphate (about $0.4$–$1.2 \times 10^{-6}M$) together with the $TxA_2$ mimetic agent, U46619.

By way of illustration, the compound described in Example 1 hereafter possesses a $pA_2$ of 8.9 in procedure (a) (U46619) and exhibits a $K_B$ of $1.2 \times 10^{-8}M$ in procedure (b) above.

In general, compounds of formula I show significant $TxA_2$ antagonist properties in one or more of the above mentioned tests i.e. test (a) $pA_2 > 6.0$; test (b) $K_B > 5 \times 10^{-6}$; test (c) dose ratio $> 5$ at 100 μg/kg p.o. In addition compounds of formula I may show significant activity in the rat blood pressure test and/or in one or more of the ex vivo blood platelet tests referred to above. No significant adverse effects have been observed at the active doses in vivo.

As stated previously, the compounds of formula I may be used in the therapy or prevention of diseases or adverse conditions in warm-blooded animals in which it is desirable to antagonise one or more of the actions of $TXA_2$. In general, a compound of formula I will be administered for this purpose by an oral, rectal, intravenous, subcutaneous, intramuscular or inhalation route, so that a dose in the range, for example 0.01–5 mg/kg body weight, will be given up to four times per day, varying with the route of administration, the severity of the condition and the size and age of the patient under treatment.

The compounds of formula I will generally be used in the form of a pharmaceutical composition comprising a compound of formula I or a pharmaceutically acceptable salt thereof as defined hereinbefore, together with a pharmaceutically acceptable diluent or carrier. Such a composition is provided as a further feature of the invention and may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; and in the form of a powder together with pharmaceutically acceptable inert solid diluents such as lactose, for administration by insufflation.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The pharmaceutical compositions of the invention may also contain one or more agents already known to be of value in the diseases or conditions intended to be treated; for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

In addition to their use in therapeutic medicine, the compounds of formula I are also useful as pharmacological tools in the development and standardisation of test systems for the evaluation of the effects of $TXA_2$ in laboratory animals such as cats, dogs, rabbits, monkeys, rats and mice, as part of the search for new therapeutic agents. The compounds of formula I may also be used because of their $TXA_2$ antagonist properties in helping to maintain the viability of blood and blood vessels in warm-blooded animals (or parts thereof) under-going artificial extracorporeal circulation, for example during limb or organ transplant. When used for this purpose a compound of formula I, or a physiologically acceptable salt thereof, will generally be administered so that a steady state concentration in the range, for example, 0.1 to 10 mg per liter is achieved in the blood.

The invention will now be illustrated by the following non-limiting Examples in which, unless otherwise stated:

(i) evaporations were carried out by rotary evaporation in vacuo;

(ii) operations were carried out at room temperature, that is in the range 18°–26° C.;

(iii) flash column chromatography was performed on Merck Kieselgel 60 (Art. 9385), monitoring the process by thin layer chromatography on Merck 0.25 mm Kieselgel 60F 254 plates (Art. 5715); these materials were obtained from E. Merck, Darmstadt, W. Germany;

(iv) yields are given for illustration only and are not necessarily the maximum attainable;

(v) NMR spectra were normally determined at 200 MHz in $CDCl_3$ using tetramethylsilane (TMS) as an internal standard, and expressed as chemical shifts (delta values) in parts per million relative to TMS using the following abbreviations for designation of major peaks; s, singlet; m, multiplet; t, triplet; br, broad; d, doublet; when a single chemical shift value is given for a multiplet (m) this corresponds to the centre point of the signals making up the multiplet; and (vi) end-products were isolated as racemates, and characterised by NMR, microanalysis, mass spectroscopy and/or other standard procedures.

EXAMPLE 1

Sodium hydride (262 mg, 50% w/w dispersion in mineral oil) was added to a stirred suspension of 4(Z)-6-([2,4,5-cis]-4-o-methoxyphenyl-2(E)-styryl-1,3-dioxan-5-yl)hexenoic acid (370 mg) in 1,3-dimethyl-3,4,5,6-tetrahydro-2(1H)-pyrimidinone (DMPU) (10 ml), maintained at 0°–5° C. After 3 minutes, ethanethiol (0.42 ml) was added and the mixture heated to 90° C. for 6 hours. The cooled mixture was diluted with water (15 ml) and washed with methylene chloride (2×25 ml). The aqueous phase was acidified to pH4 with acetic acid and extracted with diethyl ether (4×30 ml). The extracts were dried ($MgSO_4$) and evaporated. The oil thus obtained was purified by flash column chromatography on silica, eluting with toluene/ethyl acetate/acetic acid (91:9:2, by volume) to give 4(Z)-6-([2,4,5-cis]-4-o-hydroxyphenyl-2(E)-styryl-1,3-dioxan-5-yl)hexenoic acid as a crystalline solid, m.p. 138°–141° C.; NMR: 1.71 (1H, d), 1.93 (1H, d), 2.32 (4H, s), 2.72 (1H, m), 4.04 (1H, d), 4.18 (1H, d), 5.38 (3H, m), 6.27 (1H, dd), 7.17 (10H, m) and 7.92 (1H, s); m/e 394 ($M^+$).

The starting material was obtained as follows:

(E)-Cinnamaldehyde (0.41 ml) and p-toluenesulphonic acid (5 mg) were added to a solution of 4(Z)-6-(4-o-methoxyphenyl-2,2-dimethyl-1,3-dioxan-cis-5-yl)hexenoic acid (A) (700 mg) in toluene (15 ml). The mixture was stirred and heated under reflux for 1.5 hours. The cooled reaction mixture was purified by flash column chromatography on silica, eluting with toluene/ethyl acetate/acetic acid (90:10:2, by volume), to give 4(Z)-6-([2,4,5-cis]-4-o-methoxyphenyl-2(E)-styryl-1,3-dioxan-5-yl)hexenoic acid (455 mg, 53%); NMR: 1.66 (1H, m), 1.9 (1H, m), 2.27 (4H, m), 2.52 (1H, m), 3.8 (3H, m), 4.08 (2H, m), 5.3 (4H, m), 6.3 (1H, dd), 6.9 (3H, m) and 7.41 (7H, m); m/e 409 ($M^+ + H$).

The starting acid (A) was obtained as follows:

Potassium t-butoxide (12.3 g) was added over 2 minutes to a stirred suspension of (3-carboxypropyl)triphenylphosphonium bromide (23.6 g) in tetrahydrofuran (THF) (230 ml) at 0°–5° C. The mixture was stirred at ambient temperature for 30 minutes and cooled to 0° C. before the addition of (4-o-methoxyphenyl-2,2-dimethyl-1,3-dioxan-cis-5-yl)acetaldehyde (5.9 g) during 5 minutes. The mixture was stirred for 45 minutes and water (50 ml) was added. The solvent was removed by evaporation. The residue was dissolved in water (250 ml). The solution obtained was washed with ethyl acetate (3×100 ml) and acidified to pH 4 with acetic acid. The liberated oil was extracted with ethyl acetate (3×100 ml). The extracts were washed with saturated brine (2×100 ml), dried (MgSO₄) and evaporated to give an oil. The oil was purified by flash column chromatography on silica, eluting with toluene/ethyl acetate/acetic acid (80:20:1, by volume), to give 4(Z)-6-(4-o-methoxyphenyl-2,2-dimethyl-1,3-dioxan-cis-5-yl)hexenoic acid (A) as a colourless solid (6.0 g, 82%) m.p. 92°–96° C.; NMR: 1.65 (8H, m), 2.35 (5H, m), 3.85 (5H, m), 5.28 (3H, m) and 7.1 (4H, m).

EXAMPLES 2–4

Using a similar procedure to that described in Example 1, but starting from the appropriate o-methoxyphenyl derivative of formula X, the following acids of formula XI were obtained in yields of 28–80%:

| EXAMPLE | R | m.p. (°C.) | partial NMR Data |
|---|---|---|---|
| 2 | PhCH₂CH₂ | 126–128 | 2.08 (2H,m), 2.8 (2H,m), 4.75 (1H,t), 6.87 (3H,m) 7.2 (7H,m). |
| 3 | 2-Naphthyl | 44–46 | 6.87 (2H,m), 7.05 (2H,m), 7.17 (1H,m), 7.49 (2H,m), 7.65 (1H,dd), 7.85 (4H,m), 8.0 (1H,s). |
| 4 | PhCH=C.Me | oil* | 1.65 (3H,dd), 3.66 (2H,m), 4.95 (4H,m), 6.5 (3H,m), 6.85 (7H,m). |

Note:
*1:1 mixture of 'E' and 'Z' stereoisomers

The following starting materials of formula X were obtained using a similar procedure to that described in Example 1, but starting from the appropriate aldehyde of the formula R.CHO and were obtained in yields of 33–92%:

| R | State | partial NMR Data |
|---|---|---|
| PhCH₂CH₂ | oil | 2.05 (2H,m), 2.85 (2H,q), 3.8 (3H,s), 4.81 (1H,t), 6.82 (1H,d), 6.98 (1H,m), 7.23 (7H,m), 7.43 (1H,m). |
| 2-Naphthyl | oil | 3.84 (3H,s), 5.92 (1H,s), 7.92 (2H,m), 7.23 (2H,m), 7.48 (3H,m), 7.72 (1H,m), 7.87 (3H,m), 8.02 (1H,s). |
| PhCH=C.Me | oil* | 2.05 (3H,dd), 3.0 (1H,m), 3.83 (3H,d), 5.35 (4H,m), 6.7 (H,m), 6.93 (4H,m), 7.31 (7H,m). |

Note:
*Obtained an a 1:1 mixture of 'E' and 'Z' stereoisomers.

EXAMPLE 5

4-Cyano-(E)-cinnamaldehyde (150 mg), p-toluene sulphonic acid (3 mg) and 4(Z)-erythro-8-hydroxy-7-hydroxymethyl-8-o-methoxyphenyl-4-octenoic acid (294 mg) were stirred in toluene (3 ml) for 18 hours and then purified by flash column chromatography on silica. Elution with methylene chloride/ethanol (96:4, by volume), evaporation and crystallisation of the residue from n-hexane/ethyl acetate (50:50, by volume) gave as a colourless solid 4(Z)-6-([2,4,5-cis]-2-[4-cyano-(E)-styryl]-4-o-methoxyphenyl-1,3-dioxan-5-yl)hexenoic acid (110 mg, 25%) m.p. 154°–156° C.; NMR: 3.82 (3H, s), 5.3 (4H, m), 6.4 (1H, dd), 6.83 (1H, d), 6.89 (1H, d), 6.97 (1H, m), 7.25 (1H, m) and 7.55 (5H, m); m/e 433 (M+).

The necessary starting material was obtained as follow:

A solution of A (4.20 g) in a mixture of water (12 ml), 2M hydrochloric acid (0.5 ml) and THF (40 ml) was heated with stirring at 60°–70° C. After 2 hours the mixture was cooled to ambient temperature and poured into water (100 ml). The aqueous mixture was extracted with ether (3×50 ml). The combined extracts were washed successively with water (2×40 ml) and saturated brine (40 ml), then dried (MgSO₄) and evaporated to give 4(Z)-erythro-8-hydroxy-7-hydroxymethyl-8-o-methoxyphenyl-4-octenoic acid as a colourless oil (3.80 g); NMR: 1.95 (1H, m), 2.11 (1H, m), 2.37 (5H, m), 3.67 (2H, m), 3.83 (3H, s), 4.84 (3H, br), 5.22 (1H, d, J=4 Hz), 5.38 (2H, m), 6.88 (1H, br d J=7 Hz), 6.98 (1H, bt J=7 Hz), 7.25 (1H, td J=7, 1.5 Hz), 7.42 (1H, dd J=7, 1.5 Hz).

EXAMPLE 6

2-Nitro-(E)-cinnamaldehyde (107 mg) and p-toluene sulphonic acid (2 mg) were added to a stirred suspension of 4(Z)-6-(4-o-hydroxyphenyl-2,2-dimethyl-1,3-dioxan-cis-5-yl)hexenoic acid (161 mg) in toluene (2 ml). The mixture was stirred for 3 hours and then purified by flash column chromatography on silica, eluting with toluene/ethyl acetate/acetic acid (92:8:2, by volume), to give 4(Z)-6-([2,4,5-cis]-4-o-hydroxyphenyl-2-[2-nitro-(E)-styryl]-1,3-dioxan-5-yl)hexenoic acid, as a pale yellow solid (156 mg, 71%); m.p. 148°–150° C.; NMR: 1.85 (2H, m), 2.4 (4H, m), 2.65 (1H, m), 4.12 (2H, m), 5.38 (4H, m), 6.25 (1H, dd), 6.86 (2H, m), 7.13 (2H, m), 7.45 (2H, m), 7.65 (2H, m) and 7.96 (1H, dd); m/e 440 (M+ +H).

The hexenoic acid starting material was obtained as follows:

Sodium hydride (432 mg. 50% w/w dispersion in mineral oil) was added to a stirred solution of 4(Z)-6-(4-o-methoxyphenyl-2,2-dimethyl-1,3-dioxan-cis-5-yl)-hexenoic acid (500 mg) in DMPU (7.5 ml) at 0°–5° C. After 5 minutes, ethanethiol (0.66 ml) was added dropwise during 3 minutes. The mixture was maintained at 0°–5° C. for 10 minutes and then heated at 135°–140° C. for 50 minutes. The cooled reaction mixture was diluted with water (15 ml) and then washed with methylene chloride (2×30 ml). The aqueous phase was acidified to pH 4 with acetic acid and extracted with diethyl ether (4×30 ml). The ether extracts were dried (MgSO₄) and evaporated. The oil obtained was purified by flash column chromatography on silica, eluting with toluene-/ethyl acetate/acetic acid (80:20:2, by volume), to give 4(Z)-6-(4-o-hydroxyphenyl-2,2-dimethyl-1,3-dioxan-cis-5-yl)hexenoic acid, as a colourless solid (95 mg, 31%), m.p. 85°–89° C.; NMR: 1.6 (7H, m), 1.82 (1H, m), 2.32 (5H, m), 2.7 (1H, m), 3.83 (1H, dd), 4.12 (1H, gg), 5.24 (3H, m), 6.88 (3H, m), 7.17 (2H, m) and 8.47 (1H, s); m/e: 320 (M+).

EXAMPLES 7-10

Using a similar procedure to that described in Example 6, but starting from the appropriate aldehyde the following hexenoic acids of formula XI were obtained in yields of 15–70%

| EX-AMPLE | R | m.p. (°C.) | partial NMR Data |
|---|---|---|---|
| 7 | 2-o-cyanophenyl-(E)-vinyl | 113–116 | 5.45 (4H,m), 6.43 (1H,dd), 6.84 (2H,m) 7.03 (1H,m), 7.18 (3H,m), 7.37 (1H,m), 7.62 (3H,m). |
| 8 | 4-p-cyanophenyl-(E)vinyl | 135–137 | 5.37 (4H,m), 6.35 (1H,dd), 6.86 (3H,m), 7.0 (1H,m), 7.15 (1H,m), 7.55 (4H,q). |
| 9 | 2,2-diphenyl-vinyl | 52–56 | 5.1 (1H,d), 5.4, (3H,m), 6.16 (1H,d) 6.86 (3H,m), 7.37 (11,m). |
| 10 | 1-methyl-2-phenylvinyl | oil* | 1.65 (3H,dd), 3.66 (2H,m), 4.95 (4H,m), 6.5 (3H,m) 6.85 (7H,m). |

Note:
*1:1 mixture of 'E' and 'Z' stereoisomers

The starting material 2-cyano-(E)-cinnamaldehyde used in Example 7 was prepared as follows:

A solution of lithium (77 mg) in methanol (30 ml) was added during 2 hours to a stirred suspension of 2-cyanobenzaldehyde and (1,3-dioxolan-2-yl-methyl)-triphenyl phosphonium bromide (4.71 g) in dimethylformamide (34 ml) at 85° C. The mixture was stirred at 85° C. for 6 hours, allowed to cool and poured into water (450 ml). The reaction mixture was extracted with diethyl ether (3×120 ml) and the combined ether extracts washed with saturated brine, dried (MgSO4) and evaporated. The residue was dissolved and stirred in tetrahydrofuran (30 ml) and 3M hydrochloric acid (30 ml) for 2 hours. The mixture was diluted with water (100 ml) and extracted with diethyl ether (300 ml). The ether was washed with saturated sodium hydrogen carbonate solution (2×50 ml) and saturated brine, dried (MgSO4) and evaporated. The residue was purified by flash column chromatography on silica, eluting with n-hexane/ethyl acetate (80:20:, by volume) to give as a pale yellow solid 2-cyano-(E)-cinnamaldehyde (504 mg, 45%) m.p. 107°–110° C.; NMR: 6.82 (1H, q), 7.69 (5H, m) and 9.81 (1H, d); m/e 157 (M+).

EXAMPLE 11

Illustrative pharmaceutical dosage forms include the following tablet and capsule formulations, which may be otained using standard procedures:

|  | mg/tablet |
|---|---|
| TABLET I |  |
| Compound X* | 5.0 |
| Lactose Ph. Eur | 89.25 |
| Croscarmellose sodium | 4.0 |
| Maize starch paste (5% w/v paste) | 0.75 |
| Magnesium stearate | 1.0 |
| TABLE II |  |
| Compound X* | 50 |
| Lactose Ph. Eur | 223.75 |
| Croscarmellose sodium | 6.0 |
| Maize starch | 15.0 |

-continued

|  | mg/tablet |
|---|---|
| Polyvinylpyrrolidone (5% w/v paste) | 2.25 |
| Magnesium stearate | 3.0 |
| CAPSULE |  |
| Compound X* | 10 |
| Lactose Ph. Eur | 488.5 |
| Magnesium stearate | 1.5 |

Note:
Compound X* stands for a compound of formula I, or a salt thereof, for example a compound of formula I described in any of the previous Examples.

Formulae (Description)

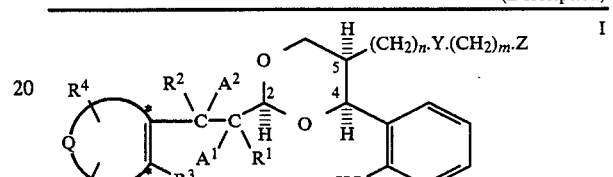

I

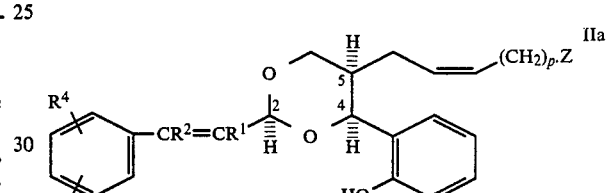

IIa

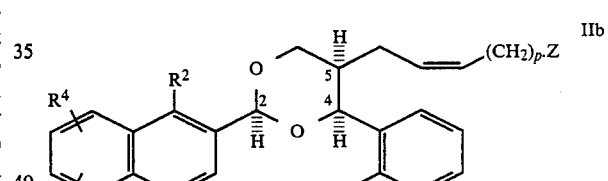

IIb

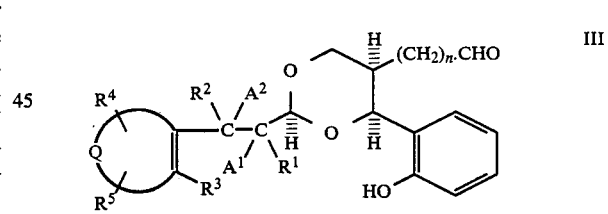

III $R_3'P=CH.(CH_2)_m.CO_2^{\ominus}M^{\oplus}$     IVa

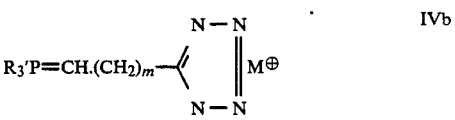

IVb $R_3'P=CH.(CH_2)_m.CO.\overset{\ominus}{N}.SO_2R^6$     IVc

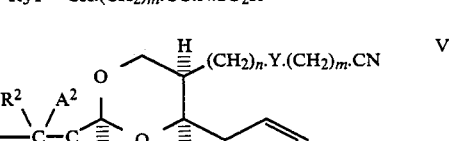

V

| Formulae (Description) | |
|---|---|
| 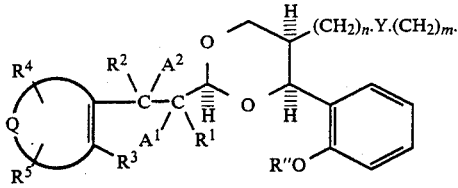 | V |
| 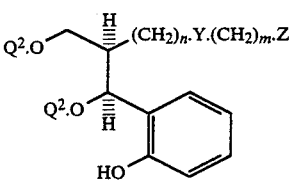 | VII |
| 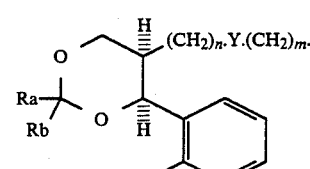 | VIII |
| 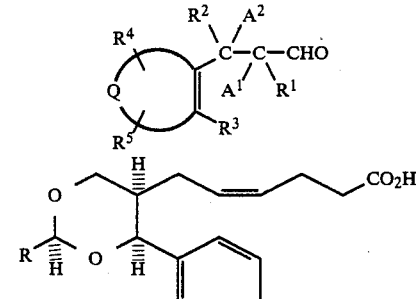 | IX |
| 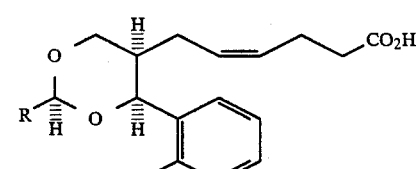 | X |
| 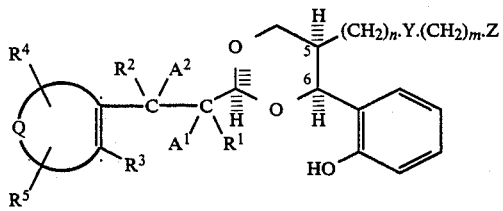 | XI |

What we claim is:

1. A (2,4,5-cis)-dioxane of the formula I

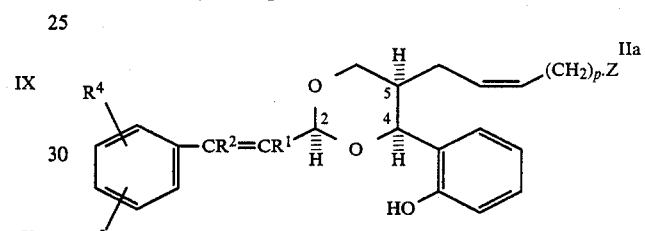

wherein $A^1$ and $A^2$ are hydrogen or together form a direct link; $R^1$ and $R^2$ are hydrogen; $R^3$ is hydrogen; $R^4$ and $R^5$ are independently selected from hydrogen, halogeno, (1-4C)alkyl, (1-4C)alkoxy, nitro, cyano, trifluoromethyl, hydroxy, (1-4C)alkanoylamino and (2-4C)alkanoyloxy, or $R^4$ and $R^5$ together form (1-4C)alkylenedioxy attached to adjacent carbon atoms in Q when the latter completes a benzene ring; Y is cis-vinylene; n is 1; m is 2; Q, in conjunction with its adjoining carbon atoms, completes a benzene or pyridine ring; and Z is carboxy, 1(H)-tetrazol-5-yl or a group of the formula —CO.NH.SO$_2$R$^6$ wherein R$^6$ is (1-6C)alkyl, benzyl or phenyl, the latter two of which are unsubstituted or bear a halogeno, (1-4C)alkyl, (1-4C)alkoxy, nitro, cyano or trifluoromethyl substituent; or a pharmaceutically acceptable salt thereof.

2. A compound as claimed in claim 1 wherein; $R^4$ and $R^5$ are independently selected from hydrogen, fluoro, chloro, bromo, methyl, ethyl, methoxy, ethoxy, nitro, cyano, trifluoromethyl, hydroxy, formamido, acetamido, acetoxy and propionyloxy, or $R^4$ and $R^5$ together form methylenedioxy or ethylenedioxy attached to adjacent carbon atoms on Q when Q completes a benzene ring; and $R^6$ is methyl, ethyl, propyl, isopropyl, benzyl or phenyl, the latter two of which are unsubstituted or bear a fluoro, chloro, bromo, methyl, ethyl, methoxy, ethoxy, nitro, cyano or trifluoromethyl substituent.

3. A styryl compound of the formula IIa

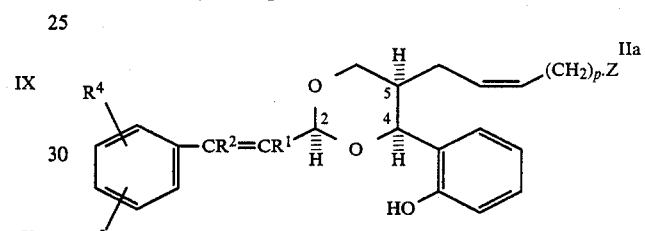

wherein $R^1$ and $R^2$ are hydrogen or; $R^4$ and $R^5$ are independently selected from hydrogen, halogeno, (1-4-C)alkyl, (1-4C)alkoxy, hydroxy, nitro, cyano and trifluoromethyl, or $R^4$ and $R^5$ together form methylenedioxy; p is 2; and Z has the meaning defined in claim 1; or a pharmaceutically acceptable salt thereof.

4. A compound as claimed in claim 1 wherein Z is carboxy.

5. A compound selected from 4(Z)-6-([2,4,5-cis]-4-o-hydroxy-phenyl-2(E)-styryl-1,3-dioxan-5-yl)hexenoic acid, 4(Z)-6-(2,4,5-cis]-2(E)-[2-cyanostyryl]-4-o-hydroxyphenyl-1,3-dioxan-5yl)hexenoic acid and the pharmaceutically acceptable salts thereof.

6. A salt as claimed in claim 1 or 3 which is selected from alkali metal, alkaline earth metal, aluminium and ammonium salts, and from salts with organic amines and quaternary bases, forming physiologically acceptable cations.

7. A method of antagonising one or more of the actions of thromboxane A$_2$ in a warm-blooded animal requiring such treatment which comprises administering to the said animal an effective amount of a compound or a pharmaceutically acceptable salt thereof, as defined in claim 1 or 3.

8. A pharmaceutical composition for use in antagonising one or more of the actions of thromboxane A$_2$ in a warm-blooded animal which comprises an effective amount of a compound, or a pharmaceutically acceptable salt thereof, as claimed in claim 1 or 3 together with a pharmaceutically acceptable diluent or carrier.

* * * * *